United States Patent
Uhlemann

(10) Patent No.: US 9,901,310 B2
(45) Date of Patent: Feb. 27, 2018

(54) PATIENT LOCALIZATION SYSTEM

(75) Inventor: Falk Uhlemann, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 217 days.

(21) Appl. No.: 14/112,044

(22) PCT Filed: Apr. 12, 2012

(86) PCT No.: PCT/IB2012/051789
§ 371 (c)(1),
(2), (4) Date: Oct. 16, 2013

(87) PCT Pub. No.: WO2012/143826
PCT Pub. Date: Oct. 26, 2012

(65) Prior Publication Data
US 2014/0037050 A1 Feb. 6, 2014

(30) Foreign Application Priority Data
Apr. 22, 2011 (EP) .................... 11163569

(51) Int. Cl.
| A61B 5/05 | (2006.01) |
| A61B 6/03 | (2006.01) |
| A61B 5/055 | (2006.01) |
| A61B 5/00 | (2006.01) |
| A61B 5/11 | (2006.01) |
| A61B 6/00 | (2006.01) |
| A61B 6/04 | (2006.01) |

(52) U.S. Cl.
CPC .............. *A61B 6/035* (2013.01); *A61B 5/055* (2013.01); *A61B 5/0507* (2013.01); *A61B 5/1113* (2013.01); *A61B 5/6892* (2013.01); *A61B 6/0492* (2013.01); *A61B 6/545* (2013.01); *A61B 6/58* (2013.01); *A61B 5/0555* (2013.01); *A61B 6/0457* (2013.01); *A61B 2562/043* (2013.01)

(58) Field of Classification Search
CPC ....... A61B 6/035; A61B 5/0507; A61B 5/055; A61B 5/1113; A61B 5/6892; A61B 6/0492; A61B 6/545; A61B 6/58; A61B 5/0555; A61B 6/0457; A61B 2562/043; A61B 6/0407; A61B 5/704
See application file for complete search history.

(56) References Cited

U.S. PATENT DOCUMENTS

| 6,405,072 B1 | 6/2002 | Cosman |
| 6,781,552 B2 * | 8/2004 | Tsai et al. ............... 343/702 |

(Continued)

FOREIGN PATENT DOCUMENTS

| DE | 102008019862 A1 | 10/2009 |
| JP | 2002058659 A | 2/2002 |
| JP | 20100178933 A | 8/2010 |

*Primary Examiner* — Long V Le
*Assistant Examiner* — Colin T Sakamoto

(57) ABSTRACT

The invention relates to means for determining the spatial configuration of a biological body (P) on a surface, particularly on the surface of a patient support (150). One embodiment of these means is a sensor system (110) that can be applied to a patient support (150) and that comprises a plurality of sensor units (111), wherein each of these sensor units (111) has an adjacent sensitive zone (112) in which the presence of a biological body (P) induces a detection signal. The sensor unit may particularly comprise a microwave coil (111).

18 Claims, 1 Drawing Sheet

(56) References Cited

U.S. PATENT DOCUMENTS

| | | | |
|---|---|---|---|
| 7,286,052 B2 * | 10/2007 | DiPoala | G08B 13/19 340/511 |
| 8,633,827 B2 | 1/2014 | Lakshminarayanan | |
| 2003/0036674 A1 * | 2/2003 | Bouton | A61B 5/05 600/12 |
| 2006/0173273 A1 | 8/2006 | Boese et al. | |
| 2006/0217612 A1 | 9/2006 | Ouchi | |
| 2009/0044334 A1 | 2/2009 | Parsell et al. | |
| 2009/0203972 A1 * | 8/2009 | Heneghan | A61B 5/0507 600/301 |
| 2009/0264735 A1 | 10/2009 | Steckner | |
| 2010/0292559 A1 * | 11/2010 | Hannemann et al. | 600/407 |
| 2010/0312104 A1 | 12/2010 | Ruchala et al. | |

* cited by examiner

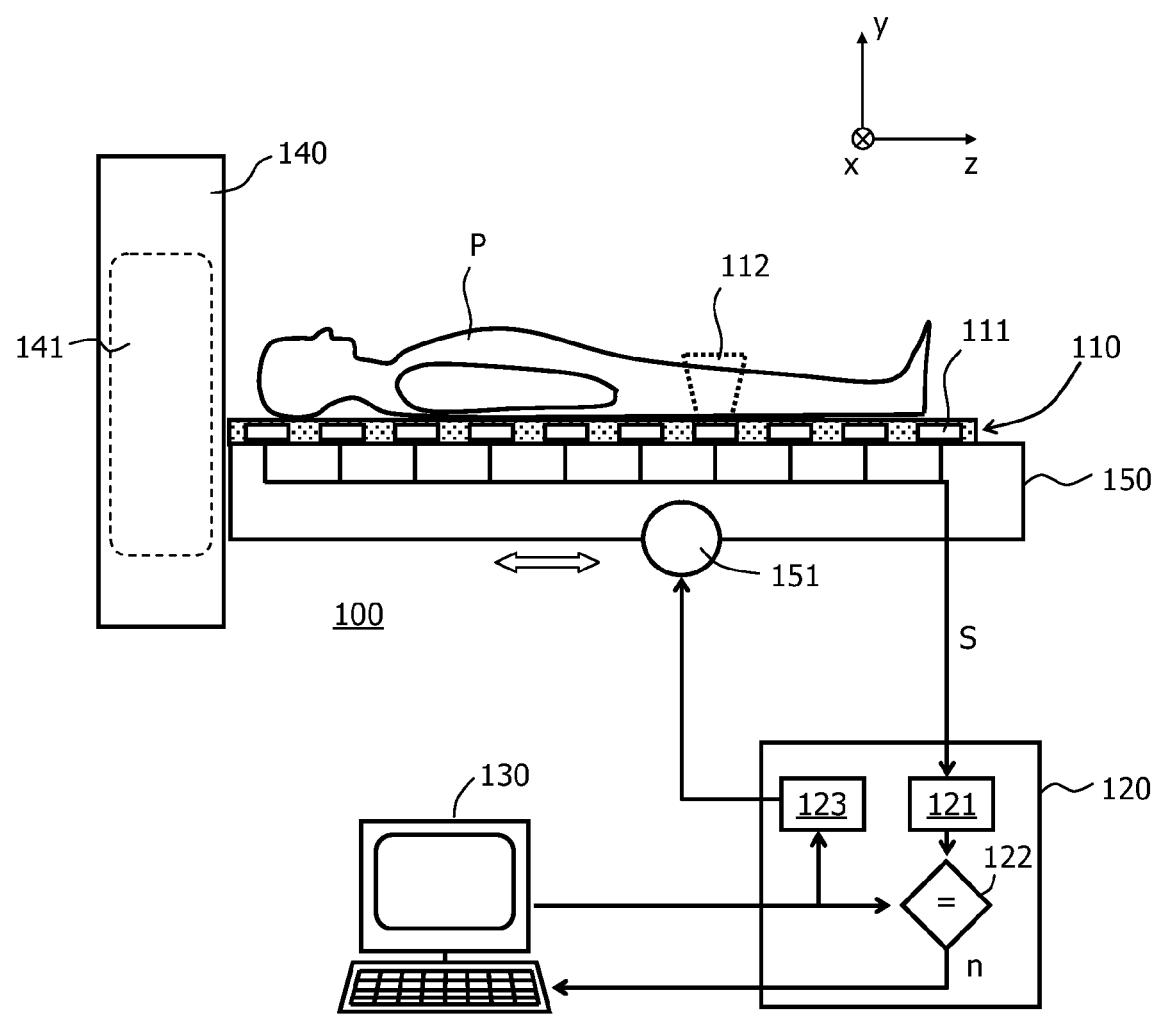

PATIENT LOCALIZATION SYSTEM

FIELD OF THE INVENTION

The invention relates to a sensor system that can be applied to a patient support, to a patient support comprising such a sensor system, to an imaging system comprising such a patient support, and to a method for determining the spatial configuration of a biological body.

BACKGROUND OF THE INVENTION

The U.S. 2009/0264735 discloses as system for detecting the position of a patient with respect to an imaging system, wherein at least one RF coil is fixed to the patient.

SUMMARY OF THE INVENTION

It is an object of the invention to provide alternative means for the localization of a patient, particularly during an imaging procedure like X-ray, CT or MR imaging.

This object is achieved by a sensor system according to claim 1, a patient support according to claim 10, an imaging system according to claim 13, and a method according to claim 15. Preferred embodiments are disclosed in the dependent claims.

According to a first aspect, the invention relates to a sensor system that can be applied to a patient support, i.e. that is integrated into such a support or laid on such a support as a separate component. The term "patient support" shall denote an element like a table or chair on which a person can sit or lie (or stand) during an examination procedure, for example during X-ray imaging. The sensor system shall comprise a plurality of sensor units, wherein each of these sensor units has an adjacent sensitive zone in which the presence of a biological body induces a detection signal of the associated sensor unit.

The sensitive zone of a sensor unit typically extends from its surface up to about 5-50 cm into the adjacent space (in a given direction). Moreover, the "induction of a detection signal by the presence of a biological body" is to be understood in such a sense that a sensor unit produces an output signal which is different depending on whether the biological body is in the sensitive zone or not. The "detection signal" may hence even comprise the vanishing of the actual output (e.g. a zero voltage) when a biological body is present, as long as this state can be distinguished from the absence of the biological body.

In a preferred embodiment, the sensor system may be realized as some kind of flexible mat into which the sensor units are integrated and that can be spread on a patient support. In this way also existing, conventional patient tables can be equipped with a sensor system according to the present invention.

According to a second aspect, the invention relates to a patient support which comprises a sensor system of the kind described above. The sensor units of said sensor system may be permanently integrated into this patient support, or they may be part of a detachable, standalone sensor system.

According to a third aspect, the invention relates to an imaging system for generating images of person, said imaging system comprising a patient support according to the second aspect of the invention. The imaging system may particularly be an X-ray device, for instance a fluoroscopic device, a Computed Tomography (CT) imaging system (e.g. a photon-counting Spectral CT imaging system), a Coherent Scatter Computed Tomography (CSCT) imaging system, a Positron Emission Tomography (PET) imaging system, a Magnetic Resonance (MR) imaging system or a Single Photon Emission Computerized Tomography (SPECT) imaging system.

According to a fourth aspect, the invention relates to a method for determining the spatial configuration of a biological body on a surface, particularly on the surface of a patient support. In this context, the term "spatial configuration" shall comprise in a general sense any spatial parameter or information relating to the biological body on the considered surface. In the most simple case, the spatial configuration may correspond to just a single value, for example the position of the centre of gravity of the biological body with respect to a given axis. In more elaborate (and typical) cases, the spatial configuration may comprise some data structure representing spatial positions of a plurality of points and/or components of the considered biological body.

The method according to the invention comprises the following steps:
Detecting the presence or absence of the biological body in a plurality of sensitive zones and producing corresponding detection signals (i.e. signals indicating the presence or absence of the body in the respective zones).
Inferring the spatial configuration of the biological body from said detection signals.

The method may particularly be executed with a sensor system of the kind described above. If the spatial configuration is a single parameter (as in the example above), the second step of the method may for example comprise the calculation of the centre of gravity of all sensitive zones in which a presence of the biological body was detected. If the spatial configuration is a more elaborate data structure, said method step may comprise the registration of the detection signals with an anatomical model of the biological body or other previously acquired data e.g. imaging data.

The sensor system, the patient support, the imaging system, and the method defined above are based on the common concept that separate sensor units are used for determining the spatial configuration of a biological body on a surface. Explanations and definitions provided for one of these embodiments are therefore analogously valid for the other embodiments, too. An essential advantage of the invention is that the spatial configuration (e.g. the position and/or posture) of a patient on a patient support can be determined in a reliable way without a laborious application of obstructive markers to the patient. Furthermore, there is no need to always guarantee a free line of sight (as it is the case for camera-based systems), because the configuration is determined with respect to adjacent sensitive zones of sensor units.

In the following, various preferred embodiments of the invention will be described that relate to the sensor system, the patient support, the imaging system, and the method defined above.

In general, the sensor units may be arbitrarily arranged as long as the desired detection results can be achieved. Most preferably, the sensor units are however arranged in a two-dimensional (regular or irregular) array. With such an array, an area of interest like the surface of a patient support can favorably be mapped.

The sensor units and/or their sensitive zones may in general be different from each other in type, size, and/or shape. Most preferably, the sensor units are however identical for reasons of production efficiency, yielding sensitive zones of the same size and shape. Regardless whether they have identical or different shapes, the sensitive zones are preferably arranged such that they do not (or at most partially) overlap. Thus the size of the area that is monitored by the sensor units can be maximized.

The sensor units can be realized in a variety of ways, for example as proximity sensors, as pressure or force sensors detecting the weight of a body lying on them, as thermal sensors that detect the (higher) temperature of an adjacent body etc. Most preferably, at least one of the sensor units comprises an emitter of radiation and/or a receiver for radiation coming from a biological body in the sensitive zone of said sensor unit. The radiation may particularly be some kind of radiation that interacts with the biological body and/or that is generated by the biological body.

In a preferred realization of the aforementioned embodiment, the considered at least one sensor unit is adapted to detect the absorption of emitted radiation and/or the reflection of emitted radiation by a biological body in its sensitive zone. Absorption of radiation emitted by the sensor unit may for example be detected via an increased consumption of energy by the considered sensor unit. Reflection of radiation emitted by the sensor unit can be used if the biological body of interest is at least partially reflective for the applied type of radiation and if there is a receiver for detecting the reflected radiation.

According to another embodiment of the invention, the detection signal that is induced in at least one sensor unit by a biological body in the sensitive zone of this sensor unit depends upon material parameters of said biological body. These material parameters may for example be related to the density of the biological body, its temperature, its electrical conductivity, or its chemical composition. The chemical composition may especially comprise values relating to the presence or absence of metal, to the water content of the biological body, or to the muscle/fat ratio.

If at least one sensor unit comprises an emitter of radiation or a receiver for radiation, this radiation may particularly be microwave radiation. By definition, microwave radiation is electromagnetic radiation with a wavelength between about 1 mm and about 100 cm. Emission of microwave radiation may particularly be achieved by a coil which is supplied with an alternating voltage of appropriate frequency. Microwave radiation is favorable in that it can readily be controlled, is harmless for a patient, has a limited reach of typically several centimeters, and interacts with biological tissue. Thus it is possible to base the detection on the absorption and/or on the reflection of microwave radiation by the biological body. Moreover, it is additionally possible to derive more detailed material parameters of a biological body with microwave radiation.

When the present invention is applied in combination with an imaging system, the sensor units are preferably designed such that they are invisible for this system when it generates its images. This can be achieved by arranging the sensor units out of the field-of-view of the imaging system. As a second alternative, the sensor units can be designed such that do not (or only little) interact with the imaging modality. In case of an X-ray imaging system, the sensor units may for example be X-ray transparent. The second alternative has the advantage that the sensor units can be brought into the field-of-view without disturbing the generated images, thus allowing to control the spatial configuration of the imaged biological body in a region where it is most necessary. Other alternatives are to characterize the interaction (e.g. absorption) with the imaging system and integrate this information for numerical compensation or to minimize the degree of interaction during imaging (e.g. via switching or detuning of sensors).

In a further development of the invention, a given target region of the biological body is localized with respect to the patient support. The localization may be expressed with respect to coordinates referring to the patient support and/or with respect to absolute coordinates referring to the environment (laboratory). The target region may for example be the centre of gravity of the biological body. Typically, it is however a more complex structure or entity, for example a particular anatomic region like the head, the chest, or a knee of a patient. The localization of such more complex target regions from the detection signals provided by the sensor units typically requires the use of an anatomical model for the biological body, which is registered with the measured detection signals (i.e. variable parameters of the model are adjusted such that a body with a corresponding configuration lying on the patient support would produce the observed detection signals). Once a spatial configuration of the model that is (sufficiently) in accordance with the measurement data has been determined, the target region of interest can readily be localized from this model.

According to a further development of the aforementioned embodiment, a warning signal may be issued if the determined target region is not located at a given absolute spatial position. The target region may for example indicate the part of the body that shall be X-rayed, and the given absolute spatial position may indicate the viewing field of the associated X-ray imaging system. The warning signal would then indicate that the region of interest is not in the field-of-view, which helps to avoid the generation of bad images. Thus both burden for the patient and costs can be reduced.

The patient support is preferably movable with at least one degree of freedom, most preferably with several degrees of freedom (e.g. with respect to axial direction, lateral direction, height, and/or inclination). This allows to bring a patient on the support into an appropriate position with respect to an examination apparatus, for example an X-ray imaging device. Most preferably, such a movable patient support comprises means for determining its absolute spatial position. As known to a person skilled in the art, such means may for instance be realized by position sensors at the bearing of the table, by optical tracking means or the like (cf. US-2010/0312104 for further examples). When the spatial configuration of a patient is known with respect to the patient support (from the detection signals of the sensor units) and the absolute spatial position of the support is known, then also the absolute (!) spatial configuration of the patient can be determined. This allows for example to verify if a target region of a patient on a movable patient support is correctly in the field-of-view or not.

According to a further development of a movable patient support, the support further comprises a controller for moving the patient support such that a given target region of a biological body on the table is moved to a given absolute spatial position. The body region that shall be imaged can thus automatically be placed in the field-of-view of the corresponding imaging system.

BRIEF DESCRIPTION OF THE DRAWINGS

These and other aspects of the invention will be apparent from and elucidated with reference to the embodiments described hereinafter.

In the sole drawing:

FIG. 1 schematically shows an imaging system according to the present invention.

DETAILED DESCRIPTION OF EMBODIMENTS

Radiation dose involved with CT and conventional X-ray procedures has become a very import issue. Field studies have shown that wrong patient positioning leads to unnecessarily repeated imaging procedures in numerous cases. This is mainly due to the complexity of imaging procedures and technology and increased workload for medical staff.

In the state of the art, positioning of patients relative to a field-of-view is done manually with laser or light field assistance. Current imaging devices can however not verify the correct positioning of the table and/or the patient.

In view of this, it is proposed to use sensor units that are integrated into or attached to the top of a patient table and detect the patient pose/position. The sensor units may particularly be microwave coils. After specification of a target region (as part of the data entry during imaging preparation), signal processing routines may compare the specified target region and the patient position setup. In case of a misalignment, the operator may be warned.

FIG. 1 schematically shows an X-ray imaging system 100 that is designed according to the above principles. The imaging system 100 comprises the following components:

- A sensor system 110 comprising a regular two-dimensional array of (identical) sensor units, here microwave coils 111. Each sensor unit 111 is sensitive in an adjacent sensitive zone 112 (indicated for one representative sensor unit only). If a biological body like a patient P is within a sensitive zone 112, the associated sensor unit produces a corresponding detection signal (or, more generally, the continuously produced signal of this sensor unit changes in a definite way).
- A patient table or support 150 that is movable by a motor 151 at least in axial direction (z-direction). Typically, the patient table 150 is also movable in lateral direction (x-direction) and vertical direction (y-direction). Furthermore, it can optionally be tilted about one or two axes. Appropriate sensors, which may for example be integrated into the motor 151, allow to determine the actual spatial position of the patient table 150 with respect to absolute x,y,z-coordinates. The array 110 of microwave coils 111 is integrated into the top of the patient table 150 over its full length.
- An imaging apparatus 140 with which images of a patient P or parts of his/her body can be generated if the latter is brought into the field-of-view 141 of said apparatus. The imaging apparatus may for example be a CT-scanner.
- An evaluation and control unit 120 which receives and processes the signals S from the microwave sensors 111. This unit may for example be realized by dedicated electronic hardware, by digital data processing hardware with associated software, or a mixture of both. The subunits that are indicated in the FIGURE shall represent different conceptual modules rather than separate hardware components.
- A user interface, for example a computer or console 130, which can exchange information with the evaluation and control unit 120.

The evaluation and control unit 120 allows to detect patient position and pose from the received detection signals S in an associated processing module 121. As part of the imaging setup on the console 130, the operator may enter the imaging target region (e.g. knee, chest). The target region specification may also occur earlier in the clinical workflow (e.g. by the referring physician). This input is then compared with the patient's position on the table in a comparison module 122. If a mismatch between the specified target region and the patient/table position occurs, a warning signal is created and transmitted to the console 130.

Optionally, the evaluation and control unit 120 may also propose the correct patient table position to an operator based on the specified target region. As indicated in the FIGURE, it may even comprise a module 123 for controlling the motor 151 of the patient table 150 such that the target region is automatically moved into the field-of-view 141 of the imaging apparatus 140.

Microwave technology is preferred to optical techniques (e.g. cameras) because it can be integrated into the table and is not disturbed by lighting conditions, patient clothing or blankets. Moreover, the microwave coils 111 can be designed X-ray transparent and very thin. Thus they can for instance be incorporated into a mat which can be attached to the table and registered with the device's coordinate system as an upgrade to existing imaging systems.

In summary, the invention allows to monitor patient position and to alert the operator in case of suspected misalignment. This is achieved via the integration of (e.g. microwave) detection technology into the patient table and subsequent signal-processing to determine the patient's pose and position. Thus accurate patient positioning can be achieved, particularly for CT and conventional X-ray imaging procedures, where it is essential for diagnostic outcome and dose minimization. The invention can also be applied for other imaging modalities (e.g. SPECT, PET, MR) to improve workflow and increase patient safety.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An imaging system for generating images of a person, comprising:
    a patient support comprising a sensor system that comprises a plurality of sensor units, wherein each of these sensor units includes a microwave coil configured with an adjacent sensitive zone in which the presence of a biological body induces a detection signal that distinguishes between the presence of the biological body and an absence of the biological body, wherein each microwave coil is configured with the adjacent sensitive zone, wherein the adjacent sensitive zone extends from a surface of each sensor unit to 50 cm away from a surface of each sensor unit in a direction extending from a surface of the patient support and towards the patient positioning region, and each adjacent sensitive zone at most partially overlaps other adjacent sensitive zones.

2. The imaging system according to claim 1, wherein the sensor units are arranged in a two-dimensional array.

3. The imaging system according to claim 1, wherein the sensor unit is adapted to detect the absorption and/or reflection of emitted radiation.

4. The imaging system according to claim 1, wherein the sensor units sense microwave radiation.

5. The imaging system according to claim 1, wherein the detection signal that is induced in at least one sensor unit by a biological body depends on material parameters of said biological body.

6. The imaging system according to claim 1, further including:
   an evaluation and control unit which localizes a given target region of a biological body and includes digital data processing hardware with associated software.

7. The imaging system according to claim 6, wherein the evaluation and control unit issues a warning signal if the target region is not located at a given absolute spatial position.

8. The imaging system according to claim 1, wherein the patient support is movable with at least one degree of freedom.

9. The imaging system according to claim 8, wherein the patient support comprises a controller for moving the patient support such that a given target region of a biological body is moved to a given absolute spatial position.

10. The imaging system according to claim 1, wherein the sensor units are invisible for the imaging system.

11. The imaging system according to claim 1, further comprising:
   an imaging apparatus selected from a group consisting of:
      an X ray device;
      a Computed Tomography (CT) imaging system;
      a Coherent Scatter Computed Tomography (CSCT) imaging system;
      a Positron Emission Tomography (PET) imaging system;
      a Magnetic Resonance (MR) imaging system; and
      a Single Photon Emission Computerized Tomography (SPECT) imaging system.

12. The imaging system according to claim 11, wherein the X ray device includes a fluoroscopic device.

13. The imaging system according to claim 11, wherein the CT imaging system includes a photon-counting Spectral CT imaging system.

14. The imaging system according to claim 1, wherein the adjacent sensitive zones of the plurality of sensor units are non-overlapping.

15. The imaging system according to claim 1, wherein the adjacent sensitive zones of each sensor unit extends from the surface of each sensor unit to 5 cm away from a surface of each sensor unit in a direction extending from the surface of the sensor system perpendicular and away from the surface of the patient support and towards the patient positioning region.

16. A method for determining the spatial configuration of a biological body on a surface of a patient support of an imaging system for generating images of a person, comprising:
   detecting with a plurality of sensor units the presence or absence of the biological body in a plurality of sensitive zones of the patient support of the system, wherein each sensor unit includes a microwave coil, wherein each sensor unit producing corresponding detection signals, wherein each microwave coil is configured with the sensitive zone, wherein the sensitive zone extends from a surface of each sensor unit and 50 cm away from the surface of each sensor unit in a direction extending from the surface of the sensor system perpendicular and away from the surface of the patient support and towards the patient positioning region;
   determining with an evaluation and control unit the spatial configuration of the biological body from said detection signals, wherein the evaluation and control unit includes digital data processing hardware with associated software.

17. The method according to claim 16, wherein each sensor unit senses microwave radiation.

18. The method according to claim 16, wherein the adjacent sensitive zones of each sensor unit extends from the surface of each sensor unit to 5 cm away from a surface of each sensor unit in a direction extending from the surface of the sensor system perpendicular and away from the surface of the patient support and towards the patient positioning region.

* * * * *